(12) United States Patent
Schena

(10) Patent No.: US 9,586,327 B2
(45) Date of Patent: Mar. 7, 2017

(54) HOOK AND PIVOT ELECTRO-MECHANICAL INTERFACE FOR ROBOTIC MEDICAL ARMS

(75) Inventor: Bruce M. Schena, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 2581 days.

(21) Appl. No.: 11/609,905

(22) Filed: Dec. 12, 2006

(65) Prior Publication Data

US 2007/0142971 A1 Jun. 21, 2007

Related U.S. Application Data

(60) Provisional application No. 60/752,563, filed on Dec. 20, 2005.

(51) Int. Cl.
*A61B 17/00* (2006.01)
*B25J 19/00* (2006.01)

(52) U.S. Cl.
CPC ........... *B25J 19/0029* (2013.01); *A61B 34/30* (2016.02); *A61B 34/37* (2016.02); *A61B 34/70* (2016.02);
(Continued)

(58) Field of Classification Search
CPC .. B25J 19/0059; A61B 19/22; A61B 19/2203; A61B 19/5212; A61B 2019/2223; A61B 2019/2242; A61B 2017/00477
(Continued)

(56) References Cited

U.S. PATENT DOCUMENTS 3,673,545 A 6/1972 Rundle
4,655,630 A * 4/1987 Rinehart ..................... 403/342
(Continued)

FOREIGN PATENT DOCUMENTS

DE 19844281 A1 5/2000
DE 10103067 A1 * 7/2002 ........... B05B 5/1625
(Continued)

OTHER PUBLICATIONS

U.S. Appl. No. 11/466,097 Office Action mailed Oct. 21, 2009, 20 pages.
(Continued)

*Primary Examiner* — Gary Jackson
*Assistant Examiner* — Boniface N Nganga

(57) ABSTRACT

A robotic medical system that includes a quick-connect/disconnect feature to facilitate the connecting and disconnecting of a robotic medical arm to and from a set-up arm is disclosed. The robotic medical system includes a robotic medical arm including an interface having a downward-oriented hook located at an upper portion thereof, and an electrical connector located at a lower portion thereof. The system further includes a set-up arm including an interface having an upward-oriented hook located at an upper portion thereof, and an electrical connector located at a lower portion thereof. To connect the robotic medical arm to the set-up arm, a user links the downward-oriented hook to the upward-oriented hook, and pivots the robotic medical arm until the respective electrical connectors mate with each other. To disconnect the robotic medical arm from the set-up arm, a user pivots the robotic medical arm to disconnect the electrical connectors, and then de-links the hooks.

22 Claims, 10 Drawing Sheets

(52) U.S. Cl.
CPC ............ *A61B 34/71* (2016.02); *A61B 90/361* (2016.02); *A61B 2017/00477* (2013.01)

(58) Field of Classification Search
USPC ............... 606/1; 439/247–248; 901/1–28; 318/568.11, 568.12, 568.21, 568.25
See application file for complete search history.

(56) References Cited

U.S. PATENT DOCUMENTS

| | | | |
|---|---|---|---|
| 4,664,588 A * | 5/1987 | Newell et al. ................. | 414/730 |
| 4,746,304 A * | 5/1988 | Asai ............................... | 439/248 |
| 4,812,133 A | 3/1989 | Fleak et al. | |
| 4,909,748 A | 3/1990 | Kozono et al. | |
| 5,035,396 A | 7/1991 | Krum et al. | |
| 5,071,374 A | 12/1991 | Plocek et al. | |
| 5,605,150 A * | 2/1997 | Radons et al. ................. | 600/300 |
| 5,752,845 A | 5/1998 | Fu | |
| 5,902,149 A | 5/1999 | Tashiro et al. | |
| 6,033,247 A | 3/2000 | Gregory, II | |
| 6,358,075 B1 | 3/2002 | Tischner | |
| 6,428,353 B2 * | 8/2002 | Mochizuki .................... | 439/545 |
| 6,592,387 B2 | 7/2003 | Komenda et al. | |
| 6,736,659 B1 | 5/2004 | Wu | |
| 6,739,891 B2 | 5/2004 | Itoh | |
| 6,788,018 B1 * | 9/2004 | Blumenkranz .......... | 318/568.11 |
| 7,014,486 B1 | 3/2006 | Wu et al. | |
| 7,762,825 B2 | 7/2010 | Burbank et al. | |
| 8,066,524 B2 | 11/2011 | Burbank et al. | |
| 2002/0160633 A1 * | 10/2002 | Brodsky et al. ................ | 439/67 |
| 2006/0035500 A1 * | 2/2006 | Sugita et al. ................. | 439/247 |
| 2006/0073723 A1 * | 4/2006 | Cowgill et al. ............... | 439/247 |
| 2006/0088367 A1 * | 4/2006 | Dellach .................. | B25J 15/04 403/31 |
| 2007/0142970 A1 | 6/2007 | Burbank et al. | |
| 2010/0241138 A1 | 9/2010 | Burbank et al. | |
| 2012/0124824 A1 | 5/2012 | Burbank et al. | |

FOREIGN PATENT DOCUMENTS

| | | |
|---|---|---|
| FR | 2618265 A1 | 1/1989 |
| WO | WO-9614101 A1 | 5/1996 |
| WO | WO-0022700 A1 | 4/2000 |

OTHER PUBLICATIONS

Final Office Action mailed Jan. 20, 2011, for U.S. Appl. No. 12/793,871, filed Jun. 4, 2010, 8 pages.

Non-final Office Action mailed Sep. 27, 2010, for U.S. Appl. No. 12/793,871, filed Jun. 4, 2010 , 9 pages.

Positronic Industries, Data Sheet for "Blind Mating System and Vibration Locking System, Rear Panel Mount," p. 11 of Subminiature-D Accessories Catalog, posted online Dec. 7, 2004, Internet: http://www.connectpositronic.com/downloads/pdf/c007revc1_c007-1revnc_subdaccess.pdf.

Southco, Data Sheets for Southco V7 Draw Latch Over-Center Series, 2003, pp. 80-83 of online catalog; Internet: http://www.southco.com/resources/documents/v7.en.pdf.

ATI Industrial Automation, "Automatic / Robotic Tool Changers," 2005, 2 pages. Internet: http://www.ati-ia.com/products/toolchanger/robot_tool_changer.aspx as displayed on the Wayback Machine at www.archive.org for Oct. 16, 2006.

Gottschalk, Mark A., "Dextrous Manipulator Targets Hazardous Environments," Design News Magazine, Feb. 10, 1992, pp. 140-141.

NASA, "NASA's Innovators: Building Smarter, Tougher Telerobots," NASA TechBriefs, Aug. 1991, pp. 11 and 92.

Odetics, "Odetics Dextrous Manipulator Design Brief," 2006, 8 pages. Internet: http://silicontraption.com/odetics_arm.htm.

PCT/US06/62018 International Search Report, mailed Apr. 22, 2008, 5 pages.

PCT/US06/62018 Written Opinion of the International Search Authority, mailed Apr. 22, 2008, 10 pages.

Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.

* cited by examiner

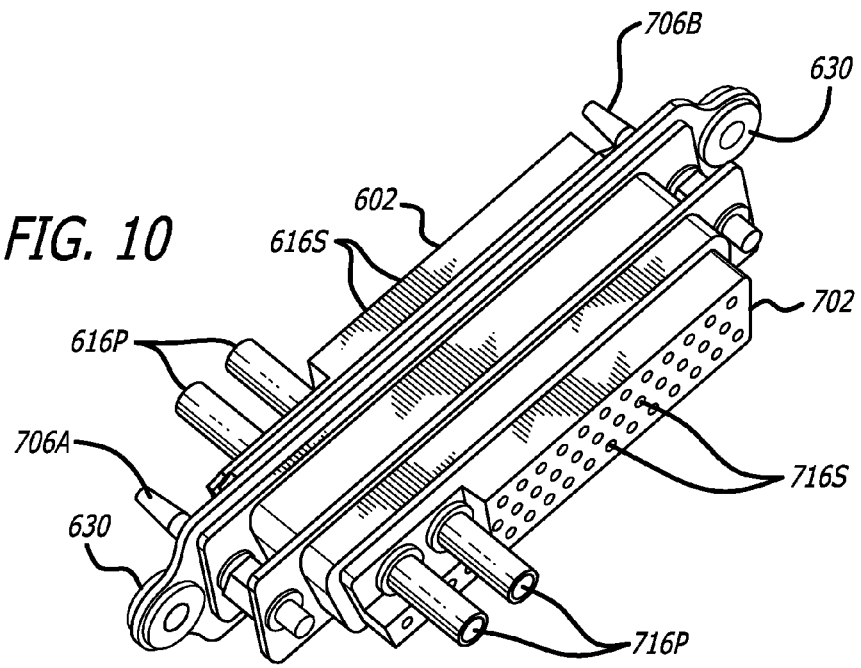
FIG. 10
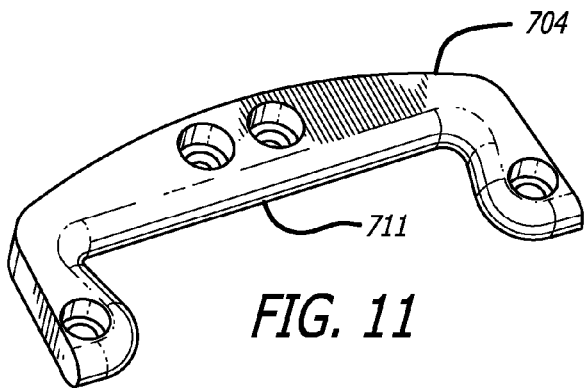
FIG. 11
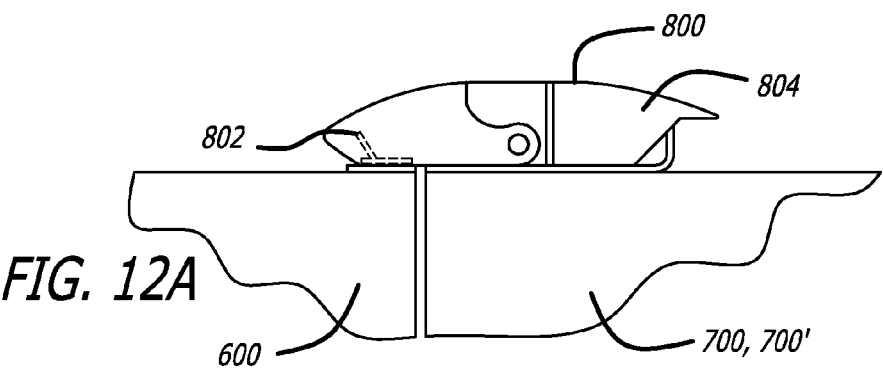
FIG. 12A
FIG. 12B

HOOK AND PIVOT ELECTRO-MECHANICAL INTERFACE FOR ROBOTIC MEDICAL ARMS

CROSS REFERENCE TO RELATED APPLICATION

This non-provisional patent application claims the benefit of U.S. Provisional Patent Application No. 60/752,563, entitled "Hook and Pivot Electro-Mechanical Interface for Surgical Robotic Arms" filed by Bruce M. Schena on Dec. 20, 2005.

FIELD

The embodiments of the invention relate generally to robotic surgical systems. More particularly, the embodiments of the invention relate to mounting and dismounting robotic surgical arms and the electro-mechanical interfaces to do so.

BACKGROUND

Robotic surgery systems are used to perform minimally invasive robotic surgical procedures. Should one of the robotic surgical arms fail for some reason, it would be desirable to replace it as quickly as possible to continue the surgery and/or perform additional procedures. If one of a plurality of robotic surgical arms of the system is not being used, it may be used to swap out the failing arm. Alternatively, a spare robotic surgical arm may be used to swap out a defective or failing robotic surgical arm. In some other cases, a robotic surgical arm may be swapped out for maintenance, adjustments, and/or cleaning. As a typical robotic surgical arm is relatively heavy, swapping out a robotic surgical arm may be difficult and time consuming for one person. Thus, there is room for improvement in robotic surgical systems to ease the swapping of robotic surgical arms into and out of a robotic surgical system.

BRIEF SUMMARY

The embodiments of the invention are summarized by the claims that follow below.

BRIEF DESCRIPTION OF THE DRAWINGS

FIG. 10 illustrates a perspective view of the electrical connector of the robotic surgical arm mated with the electrical connector of the setup joint bracket.

FIG. 11 illustrates a perspective view of the hook of the drive mount.

FIG. 12A illustrates a cut-away side view of the setup joint bracket coupled to the drive mount and fastened together by an over center latch.

FIG. 12B illustrates a side view of a keeper of the over center latch illustrated in FIG. 12A.

Figure 1:
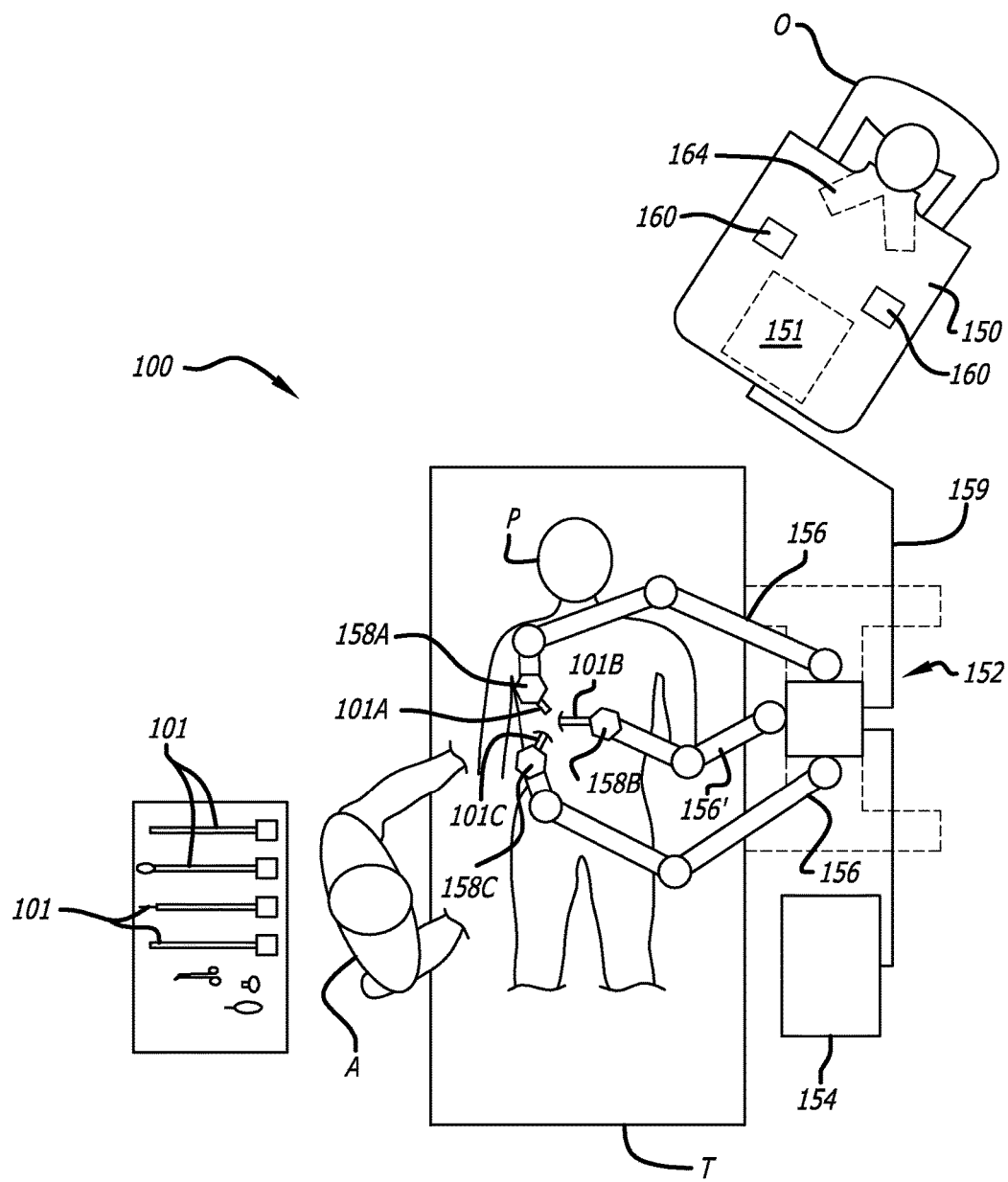
FIG. 1 is a block diagram of a robotic surgery system to perform minimally invasive robotic surgical procedures using one or more robotic surgical arms.

It will be appreciated that all the drawings of Figures provided for herein are for illustrative purposes only and do not necessarily reflect the actual shape, size, or dimensions of the elements being illustrated.

DETAILED DESCRIPTION

In the following detailed description of the embodiments of the invention, numerous specific details are set forth in order to provide a thorough understanding of the present invention. However, it will be obvious to one skilled in the art that the embodiments of the invention may be practiced without these specific details. In other instances, well known methods, procedures, components, and circuits have not been described in detail so as not to unnecessarily obscure aspects of the embodiments of the invention.

Introduction

The embodiments of the invention include methods, apparatus and systems for robotic medical systems.

In one embodiment of the invention, a robotic surgical system is provided including one or more robotic surgical arms with electro-mechanical interfaces to mount and dismount with electro-mechanical interfaces of set-up arms of a patient side system. The robotic surgical arm includes a first interface having a first hook near a first side and a first electrical connector near a second side opposite the first side. The set-up arm includes a second interface to couple to the first interface of the robotic surgical arm. The second interface has a second hook near a first side and a second electrical connector near a second side opposite the first. The first hook is adapted to link and pivot with respect to the second hook until the first electrical connector of the robotic surgical arm substantially mates with the second electrical connector of the set-up arm.

In another embodiment of the invention, a robotic surgical arm is provided that includes a plurality of links pivotally coupled together in series to maneuver a tool during surgery; a first motor coupled to at least one of the plurality of links to pivot the plurality of links; and a drive mount pivotally coupled to a first link of the plurality of links. The drive mount has a first hook and a first electrical connector positioned in different portions of an electro-mechanical interface. The first hook is to hook onto and pivot in one or more hooks of a setup joint bracket of a set-up arm. The first electrical connector is to mate with a second electrical connector of the setup joint bracket of the set-up arm to provide one or more control signals to control the first motor.

In yet another embodiment of the invention, a method of attaching a robotic surgical arm to a set-up arm in a robotic surgical system is provided. The method includes mating a first hook of a robotic surgical arm with a second hook of a set-up arm; pivoting the robotic surgical arm about a rotational axis located proximate the second hook; aligning the robotic surgical arm with the set-up arm; and securing the robotic surgical arm to the set-up arm. The method may further include aligning a first electrical connector of the robotic surgical arm with a second electrical connector of the set-up arm.

In still another embodiment of the invention, a method of detaching a robotic surgical arm from a set-up arm in a robotic surgical system is provided. The method includes removing a securing device that secures a robotic surgical arm to a set-up arm; pivoting the robotic surgical arm about a rotational axis located proximate a linked pair of hooks located respectively at upper portions of respective first and second interfaces of the robotic surgical arm and the set-up arm; and de-linking the hook of the first interface from the hook of the second interface. The pivoting may disconnect a first electrical connector located at a lower portion of the first interface from a second electrical connector located at a lower portion of the second interface.

Robotic Surgical System

Referring now to FIG. 1, a block diagram of a robotic surgery system 100 is illustrated to perform minimally invasive robotic surgical procedures using one or more robotic arms with strap drive. Robotic surgery generally involves the use of a robot manipulator that has multiple robotic manipulator arms. One or more of the robotic manipulator arms often support a surgical tool which may be articulated (such as jaws, scissors, graspers, needle holders, micro dissectors, staple appliers, tackers, suction/irrigation tools, clip appliers, or the like) or non-articulated (such as cutting blades, cautery probes, irrigators, catheters, suction orifices, or the like). At least one of the robotic manipulator arms (e.g., the center robotic manipulator arm 158B) is used to support a stereo or three dimensional surgical image capture device, such as a stereo endoscope (which may be any of a variety of structures such as a stereo laparoscope, arthroscope, hysteroscope, or the like), or, optionally, some other stereo imaging modality (such as ultrasound, fluoroscopy, magnetic resonance imaging, or the like). Robotic surgery may be used to perform a wide variety of surgical procedures, including, but not limited to, open surgery, neurosurgical procedures (such as stereotaxy), endoscopic procedures (such as laparoscopy, arthroscopy, thoracoscopy), and the like.

A user or operator O (generally a surgeon) performs a minimally invasive surgical procedure on patient P by manipulating control input devices 160 at a master control console 150. A computer 151 of the console 150 directs movement of robotically controlled endoscopic surgical instruments 101A-101C by means of one or more control cables 159, effecting movement of the instruments using a robotic patient-side system 152 (also referred to as a patient-side cart). The robotic patient-side system 152 has one or more robotic arms 158A-158C. In one embodiment of the invention, the one or more robotic arms 158A-158C have a strap drive system. Typically, the robotic patient-side system 152 includes at least three robotic manipulator arms 158A-158C supported by linkages of the set-up arms 156, 156', with a central robotic arm 158B supporting an endoscopic camera 101B and the robotic arms 158A, 158C to left and right of center supporting tissue manipulation tools 101A and 101C.

Generally, the robotic patient-side system 152 includes a positioning portion and a driven portion. The positioning portion of the robotic patient-side system 152 remains in a fixed configuration during surgery while manipulating tissue. The driven portion of the robotic patient-side system 152 is actively articulated under the direction of the operator O generating control signals at the surgeon's console 150 during surgery. The actively driven portion of the robotic patient-side system 152 is generally referred to herein as the robotic arms or alternatively to robotic surgical manipulators. The positioning portion of the robotic patient-side system 152 that is in a fixed configuration during surgery may be referred to as "set-up arms" 156, 156' with positioning linkage and/or "set-up joints" (SUJ). In an alternate embodiment of the invention, the robotic patient-side system 152 may be replaced by set-up arms that couple at one end to left and right sides of the operating table T. The three robotic manipulator arms 158A-158C may then be coupled to the opposite end of the set-up arms.

For convenience in terminology, manipulators such as robotic surgical arms 158A and 158C actuating the tissue affecting surgical tools 101A and 101C are generally referred to herein as a PSM (patient-side manipulators), and a robotic surgical arm 158B controlling an image capture or data acquisition device, such as the endoscopic camera 101B, is generally referred to herein as a ECM (endoscopic camera manipulator), it being noted that such telesurgical robotic manipulators may optionally actuate, maneuver and/or control a wide variety of instruments, tools and devices useful in surgery. The surgical tools 101A, 101C and endoscopic camera 101B may be generally referred to herein as tools or instruments 101.

An assistant A may assist in pre-positioning of the robotic patient-side system 152 relative to patient P as well as swapping tools or instruments 101 for alternative tool structures, and the like, while viewing the internal surgical site via an assistant's display 154. With the embodiments of the invention, the assistant A may also swap in and out the robotic surgical arms 158A and 158C, as well as the robotic surgical arm 158B, in case one is defective or failing. In other cases, a robotic surgical arm may be swapped out for maintenance, adjustments, or cleaning and then swapped back in by one or more service persons.

Figure 2:
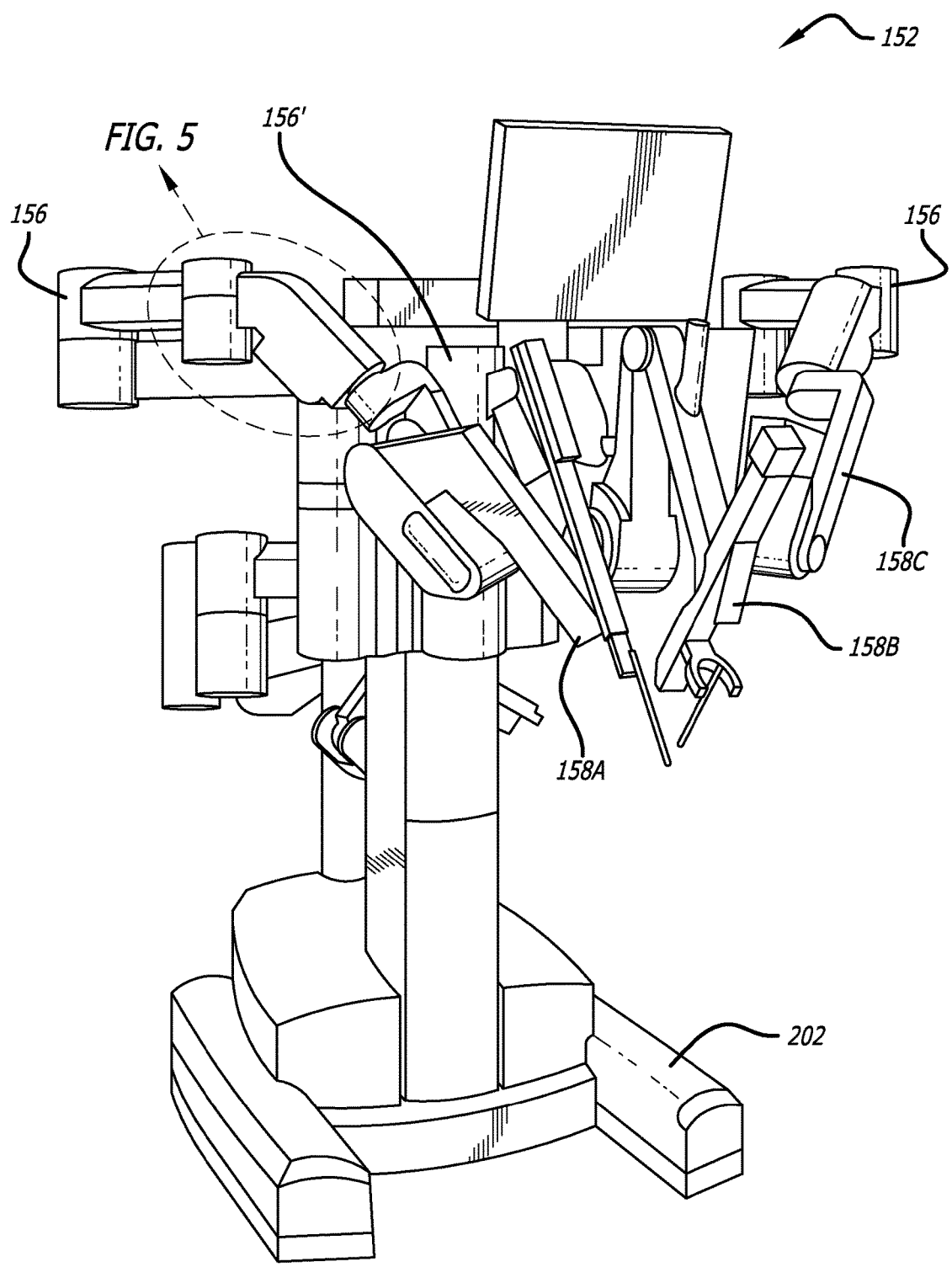
FIG. 2 a perspective view of the robotic patient-side system of FIG. 1 with the one or more robotic surgical arms having the strap drive train.

Referring now to FIG. 2, a perspective view of the robotic patient-side system 152 is illustrated. The robotic patient-side system 152 may have one or more robotic surgical arms (a.k.a., robotic surgical manipulators) 158A-158C. The robotic arms 158A,158C are for coupling to robotic surgical tools 101A, 101C and may also be referred to as patient side manipulators (PSM). The robotic arm 158B is for coupling to an endoscopic camera 101B and may also be referred to as an endoscopic camera manipulator (ECM). Generally, the surgical robotic arms 158A-158C may be referred to as a surgical robotic arm or a robotic surgical arm.

The robotic patient-side system 152 further includes a base 202 from which the robotic surgical instruments 101 may be supported. More specifically, the robotic surgical instruments 101 are each supported by the positioning linkage of the set-up arms 156 and the surgical robotic arms 158.

Robotic Surgical Arms

Figure 3:
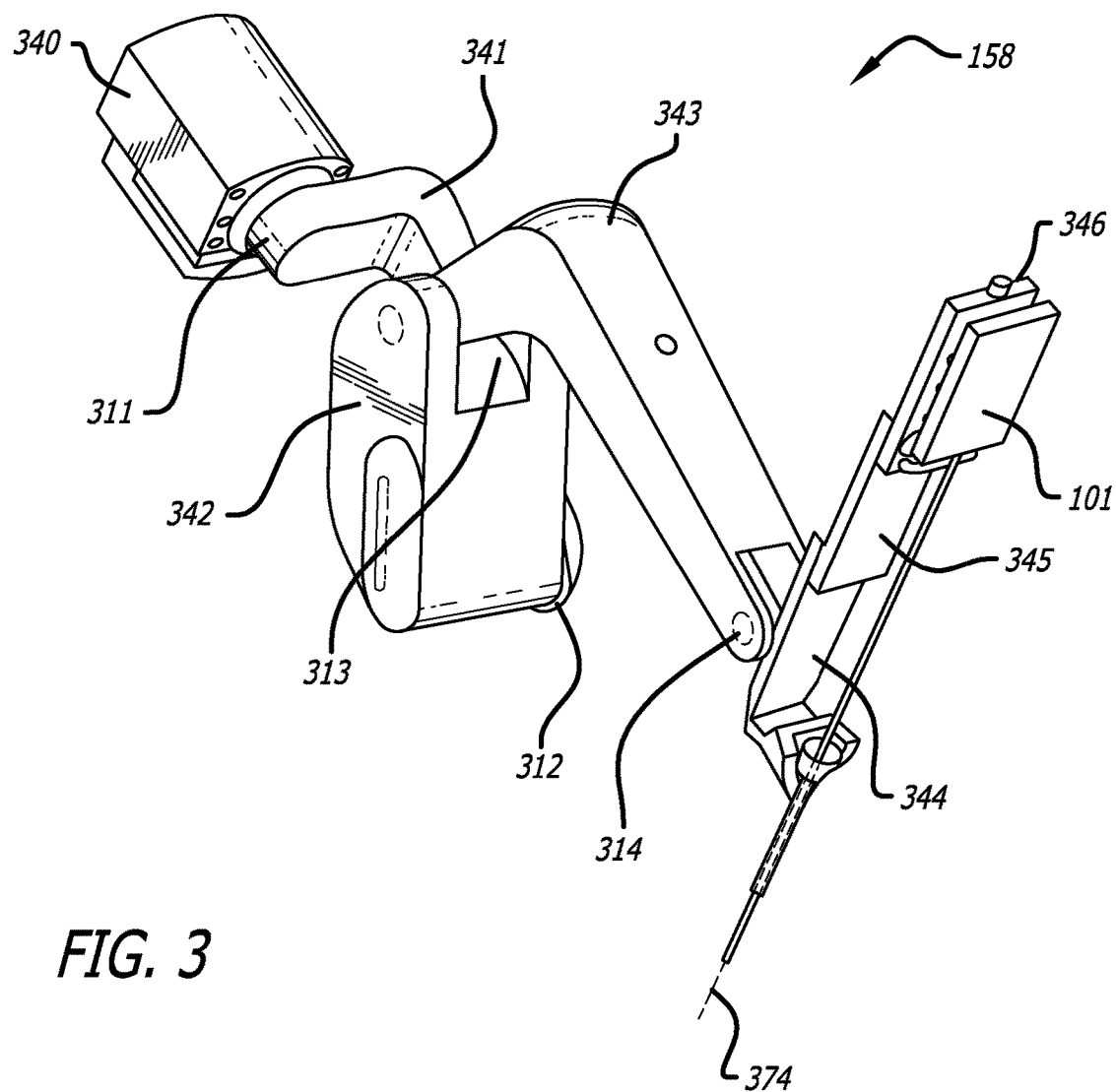
FIG. 3 is a perspective view of a robotic surgical arm.

Referring now to FIG. 3, a perspective view of a robotic surgical arm 158 is illustrated. As discussed previously, a robotic surgical tool 101 may couple to the robotic surgical arm 158. The robotic surgical arm 158 includes a plurality of serial links 341-344 pivotally coupled in series at joints 312-314 near respective ends of the links. The first link (Link 1) 341 is pivotally coupled to a drive mount 340 at a first joint 311 near a first end and the second link (Link 2) 342 at the second joint 312 near a second end. The second link 342 may house a motor to drive the linkage of the arm in one embodiment of the invention. The third link (Link 3) 343 is pivotally coupled to the second link 342 near a first end and pivotally coupled to the fourth link (Link 4) 344 near a second end. Generally, the fourth link is substantially in parallel to the insertion axis 374 of the robotic surgical tool. A fifth link (Link 5) 345 is slidably coupled to the fourth link 344. A sixth link (Link 6) 346 is slidably coupled to the fifth link 345. Various types of surgical tools 101 couple to the sixth link 346 of the robotic surgical arm.

The robotic surgical arm 158 includes the mounting base or drive mount 340 that allows it to be mounted and supported by set-up arms/joints 156 and 156' of a cart mount, ceiling mount, floor/pedestal mount, or other mounting surface of a patient-side system 152.

Figure 4:
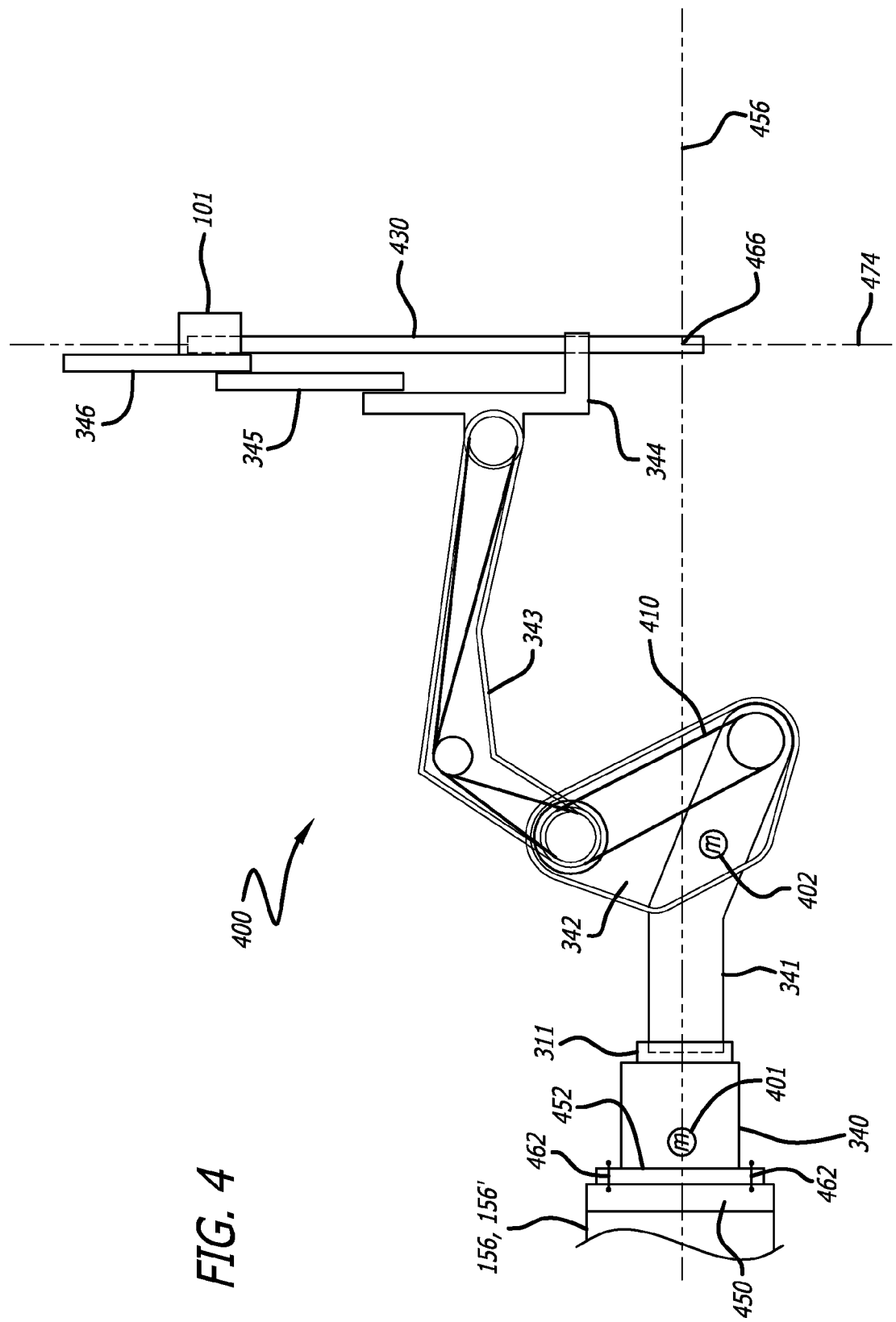
FIG. 4 is a schematic side view of a multi-strap drive train having a two-strap drive system in a third link.

Referring now to FIG. 4, a schematic diagram of a drive train 410 of a robotic surgical arm 400 is illustrated. The drive train 410 of the robotic surgical arm 400 may drive and support the weight or load of the robotic arm itself and the load that may be placed on it by the surgical tool in the surgical site.

The drive train in conjunction with the links and joints of the robotic surgical arm 400 may constrain the motion of the shaft 430 of the surgical tool relative to a center of rotation 466.

The mounting base or drive mount 340 may include a motor 401 to yaw the robotic arm 400 about the axis 456 illustrated in FIG. 4. As discussed previously and as illustrated in FIG. 4, the second link 342 may house a motor 402 to drive the linkage of the arm about a pitch axis 474.

Electro-Mechanical Interfaces

In FIG. 4, the mounting base or drive mount 340 of the surgical robotic arm 400 includes electrical and mechanical connectors 452 to mate with electrical and mechanical connectors 450 in a connector portion of a set-up joint of the set-up arm 156,156'. Additionally, fasteners 462 (such as bolts) may be used to rigidly couple the robotic surgical arm 400 to the set-up arm 156,156'. Alternatively, a lever arm may be used to lock and unlock the arm 400 from the arms 156,156' to quickly mount and dismount the robotic surgical arm from the patient side system. Including a hook and pivot electro-mechanical interface between the surgical robotic arm 400 and the set-up arm 156,156' can also assist in quickly mounting and dismounting a robotic surgical arm from a patient side system.

Figure 5:
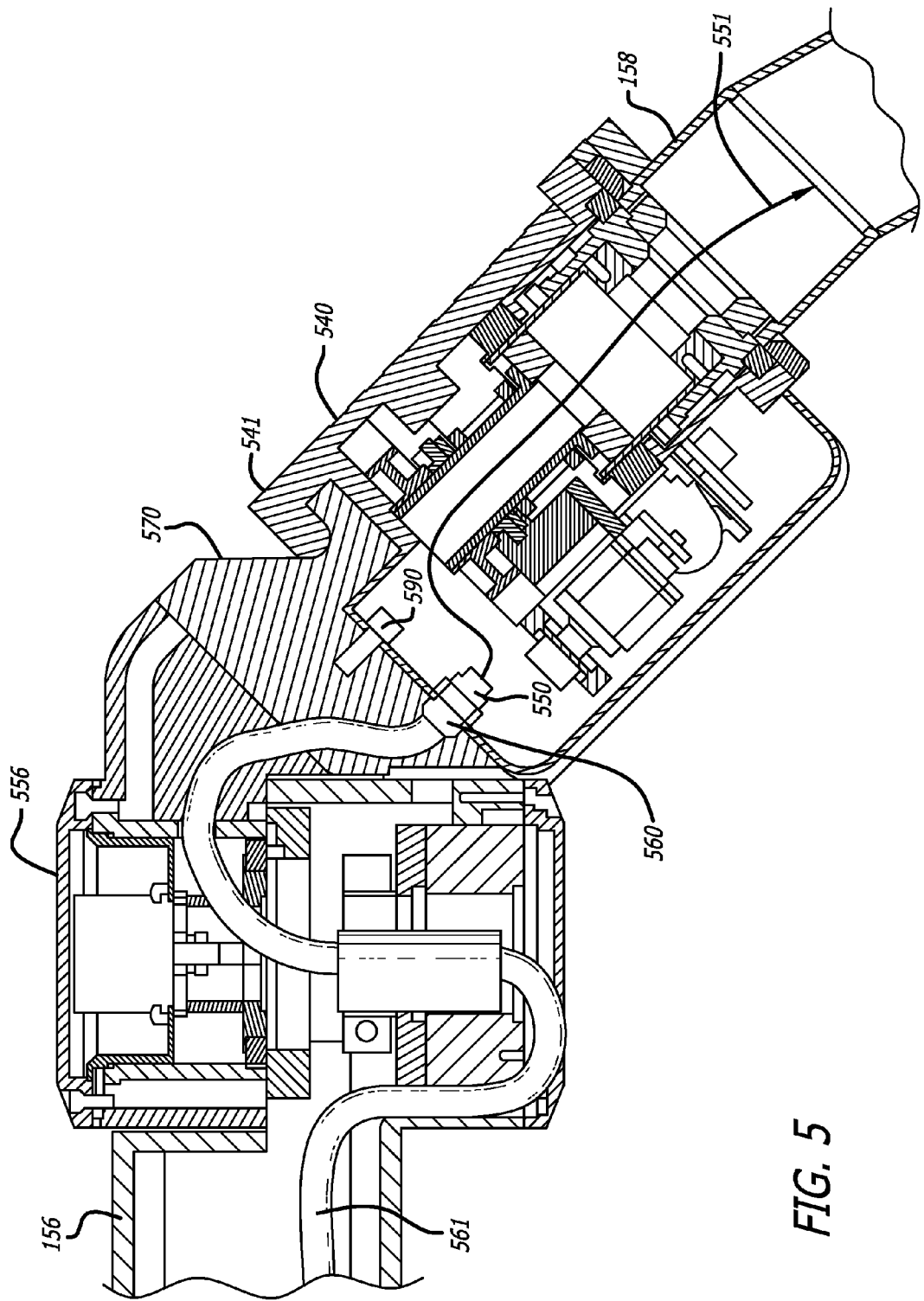
FIG. 5 is a cutaway side sectional view of a robotic surgical arm mounted to a set-up arm in a robotic surgical system.

Referring now to FIG. 5, a side sectional view of a surgical robotic arm (SRA) portion 540 of a robotic surgical arm 158 and a set-up joint (SUJ) portion 556 of a set-up arm 156,156' of the robotic patient-side system 152 is shown. Generally, the SRA portion 540 of the robotic surgical arm 158 may be mechanically and electrically coupled to the SUJ portion 556 of the set-up arm 156 as shown in FIG. 5.

The SRA portion 540 is adapted for mechanically coupling to the SUJ portion 556 of the set-up arm. An interface 541 of the SRA portion 540 can couple to an interface 570 of the SUJ portion 556. The SUJ portion 556 may also be referred to herein simply as a set-up joint 556. The SRA portion 540 may also be referred to herein previously as a drive mount 340 or a mounting base 340.

As shown in FIG. 5, the interface 541 of the SRA portion 540 may also be adapted for electrically coupling to the interface 570 of SUJ portion 556. To do so, the interface 570 of SUJ portion 556 may include one or more electrical connectors 560. The interface 541 of the SRA portion 540 may include one or more electrical connectors 550. As the interface 541 of the SRA portion 540 aligns with the interface 570 of SUJ portion 556, the electrical connectors 550 and 560 are first aligned together and then are electrically and mechanically coupled together. In one embodiment of the invention, the electrical connectors 550 in the SRA portion 540 are fixed in position and the electrical connectors 560 in the SUJ portion 556 are adjustable in position such that they can be aligned to the connectors 550. In an alternate embodiment of the invention, the electrical connectors 560 in the SUJ portion 556 are fixed in position and the electrical connectors 550 in the SRA portion 540 are adjustable in position such that they can be aligned to the connectors 560. In yet another embodiment of the invention, the electrical connectors 550 and 560 may both be adjustable in position to align and couple together.

One or more fasteners 590, 462, or 800 may be used to remove any play between the interface 541 of the SRA portion 540 and the interface 570 of SUJ portion 556. In the surgical robotic arm 158, one or more cables 551 are used to couple data signals, control signals, power, and ground from the connectors 550 to the electrical system of the surgical robotic arm 158, such as the motors 401,402. In the set-up arm 156, one or more cables 561 are used to couple data signals, control signals, power, and ground from the connectors 560 to the electrical system of the patient side system 152.

Pivotable Electro-Mechanical Interfaces

A hook and pivot electro-mechanical interface for robotic surgical arms is now described with reference to FIGS. 6A-12B.

Figure 6A:
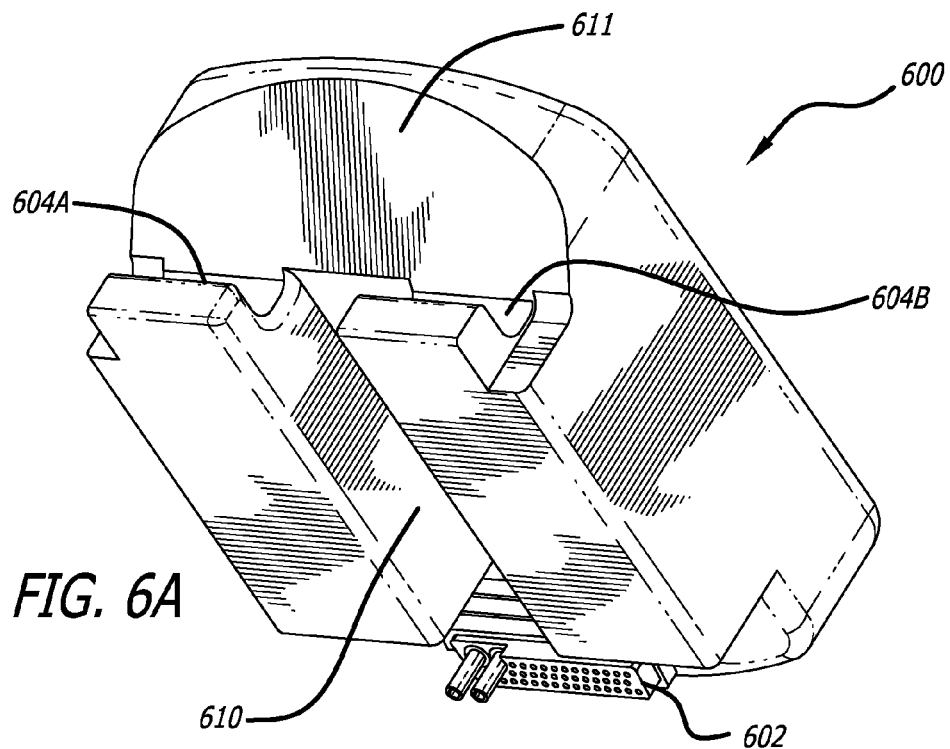
FIGS. 6A-6B illustrate views of a setup joint bracket of a set-up arm.
Figure 6B:
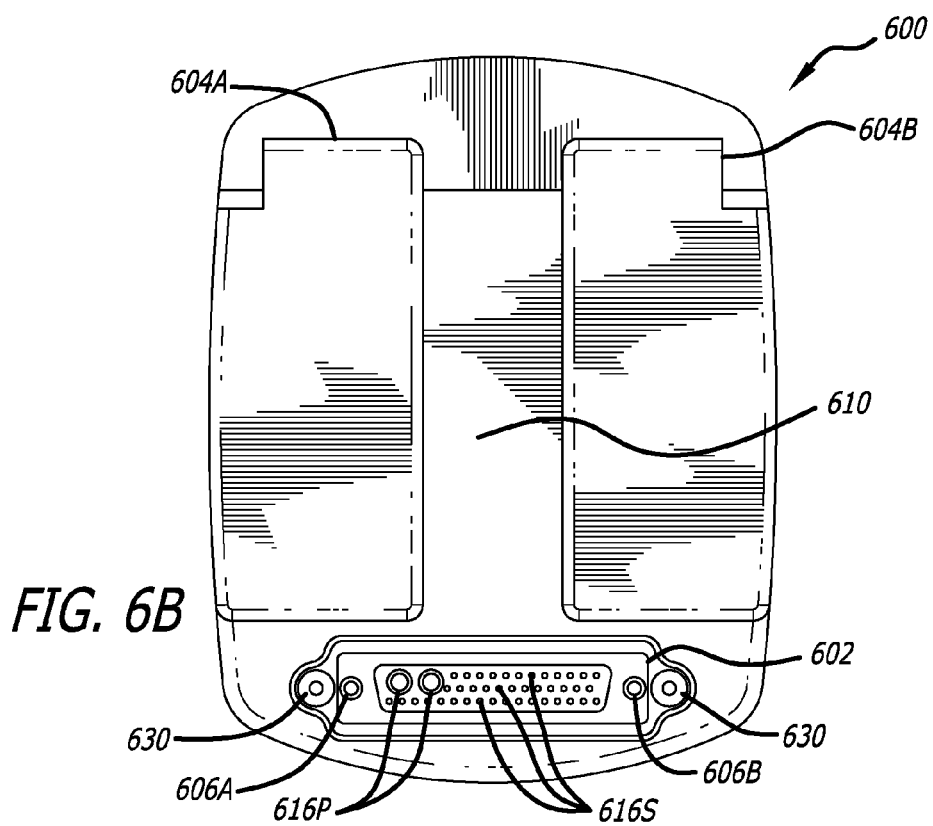

FIGS. 6A-6B illustrate a setup joint bracket 600 of a set-up arm 156, with its blind mated electrical connector 602 and one or more hooks 604A-604B to receive a corresponding hook 704 of a drive mount 700 of a robotic surgical arm 158. Hooks 604A-604B are located in a top portion of the hook and pivot electro-mechanical interface between the set-up arm 156 and robotic surgical arm 158. The setup joint bracket 600 further includes a chamfer portion 611 above one or more hooks 604A-604B as best illustrated in FIG. 6A. The chamfer 611 provides space for the drive mount 700 of the robotic surgical arm to mount the hook 704 onto the one or more hooks 604A-604B of the setup joint bracket 600 and pivot about rotational axes located near the one or more hooks 604A-604B.

As shown in FIGS. 6A-6B, the setup joint bracket 600 further includes an alignment recess, slot or opening 610 near its the center between the one or more hooks 604A-604B. An alignment protrusion or a center tapered key 710 of the drive mount 700 (shown in FIGS. 7A-7B) mates with the alignment recess, slot or opening 610 of the setup joint bracket 600 to coarsely align the robotic surgical arm 158 with the set-up arm 156.

The electrical connector 602 of the setup joint bracket 600 is a floating connector that is allowed to move slightly and couple to a more rigid electrical connector 702 of the drive mount 700 in one embodiment of the invention. The electrical connector 602 is located at a bottom portion, opposite the top portion, of the hook and pivot electro-mechanical interface between the set-up arm 156 and robotic surgical arm 158. As is also illustrated in FIG. 10, the electrical connector 602 includes a pair of floating bushings 630 to be moveable in one embodiment of the invention.

In another embodiment of the invention, the electrical connector 602 may be the more rigid electrical connector and the electrical connector 702 of the drive mount has floating bushings to be moveable to align and mate the electrical connectors together. In another embodiment of the invention, both electrical connectors 602 and 702 have floating bushings so both are movable and can align and mate the electrical connectors together Additionally, the electrical connector 602 may include alignment holes 606A-606B, as shown in FIG. 6B, to mate with tapered alignment pins 706A-706B such as is shown in FIG. 10. Furthermore, the electrical connector 602 includes a plurality of electrical signal pins 616S as shown in FIG. 6B. The electrical connector 602 may also include electrical power pins 616P in one embodiment of the invention, as shown in FIG. 6B. The electrical signal pins 616S may be female signal pins to mate with male signal pins in the electrical connector 702, in one embodiment of the invention. In another embodiment of the invention, the electrical signal pins 616S may be male signal pins to mate with female signal pins in the electrical connector 702. Similarly, the electrical power pins 616P may be female or male to respectively mate with male or female electrical power pins of the electrical connector 702. The electrical power pins 616P may be power and ground pins or a pair of power pins with ground being made through another connection.

Figure 7A:
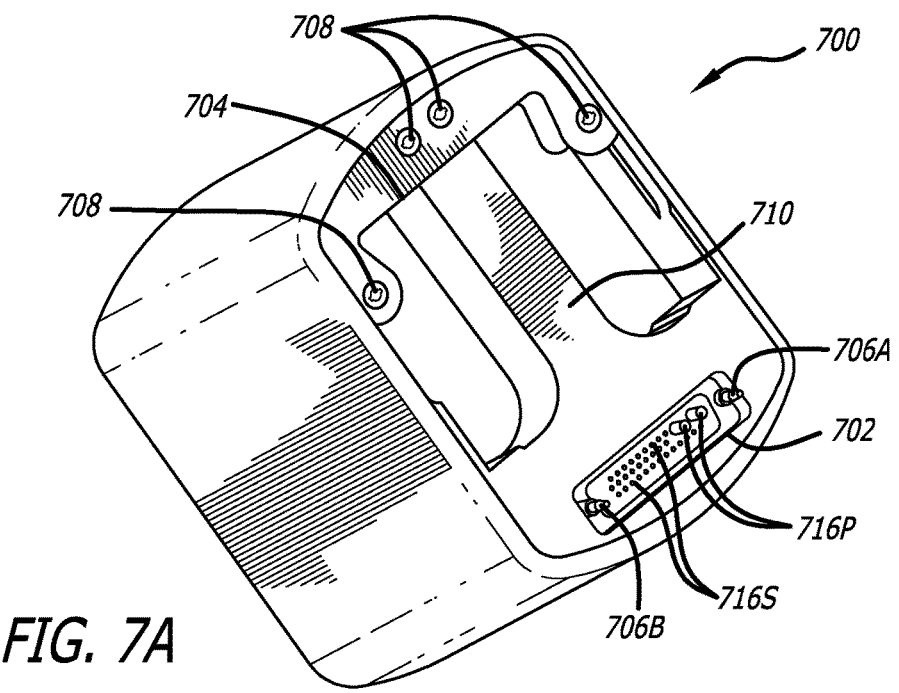
FIG. 7A-illustrates a perspective view of a drive mount for a robotic surgical arm in one embodiment of the invention.
Figure 7B:
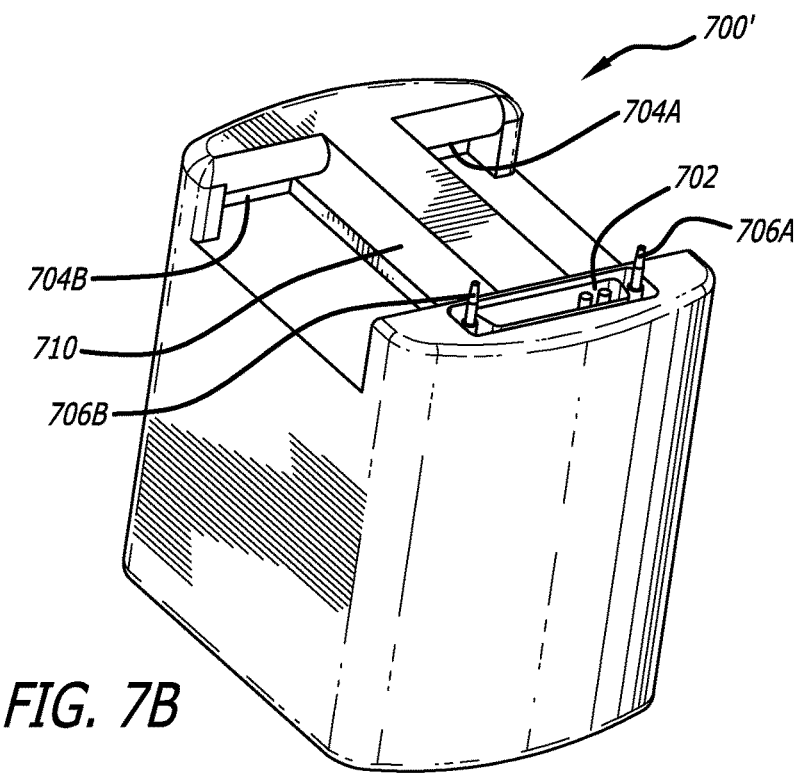
FIG. 7B illustrates a perspective view of a drive mount for a robotic surgical arm in another embodiment of the invention.

Referring now to FIGS. 7A-7B, alternate embodiments of a drive mount 700, 700' are illustrated. The drive mount 700 illustrated in FIG. 7A includes a hook 704 in a top portion and an electrical connector 702 in a bottom portion with a pair of tapered alignment pins 706A-706B. The downward-facing hook 704 of the drive mount 700 engages one or more upward-facing hooks 604A-604B of the setup joint (SUJ) bracket 600. The details of the hook 704 of the drive mount 700 are illustrated in FIG. 11.

FIG. 7B illustrates a drive mount 700', an alternate construction of the drive mount 700 as another embodiment of the invention. The drive mount 700' includes one or more hooks 704A-704B in a top portion of the interface and the electrical connector 702 in a bottom portion of the interface. The one or more hooks 704A-704B of the drive mount 700 latches over the corresponding one or more hooks 604A-604B of the setup joint (SUJ) bracket 600.

Each of the drive mounts 700,700' includes an alignment protrusion or a center tapered key 710 that aligns the robotic surgical arm and its electrical connector to the setup arm with the joint bracket 600 and its electrical connector 602. The center tapered key 710 of the drive mount 700,700' mates with the alignment recess, slot, or opening 610 of the setup joint bracket 600. The opening 610 is in center between the one or more hooks 604A-604B and the electrical connector 602 of the setup joint bracket 600. The hook 704 of the drive mount 700 is mounted into the one or more hooks 604A-604B of the setup joint bracket 600 and pivots therein at the top so that the electrical connector 702 of the drive mount 700 is pivoted into the electrical connector 602 of the setup joint bracket 600. Similarly, the one or more hooks 704A-704B of the drive mount 700' are mounted into the one or more hooks 604A-604B of the setup joint bracket 600 and pivot therein at the top so that the electrical connector 702 of the drive mount 700 is pivoted into the electrical connector 602 of the setup joint bracket 600. In this manner, an electrical coupling and a mechanical coupling are coincidentally made between the drive mount 700 and the setup joint bracket 600.

The electrical connector 702 of the drive mounts 700,700' may be a blind-mated electrical connector. As discussed previously, the electrical connector 702 may include a pair of tapered alignment pins 706A-706B to mate with alignment holes 606A-606B in the electrical connector 602 in one embodiment of the invention. Alternatively, the electrical connector 702 may have alignment holes with the electrical connector 602 having tapered alignment pins to mate therein, in another embodiment of the invention.

The electrical connector 702 has a plurality of electrical signal pins 716S as is illustrated in FIG. 7A. The electrical connector 702 may also have one or more electrical power pins 716P as illustrated in FIG. 7A. The electrical signal pins 716S and the electrical power pins 716P may be male or female pins to respectively mate with female or male pins of the electrical connector 602. The electrical power pins 716P may be power and ground pins or both power pins with ground being provided by another connection means.

Figure 8A:
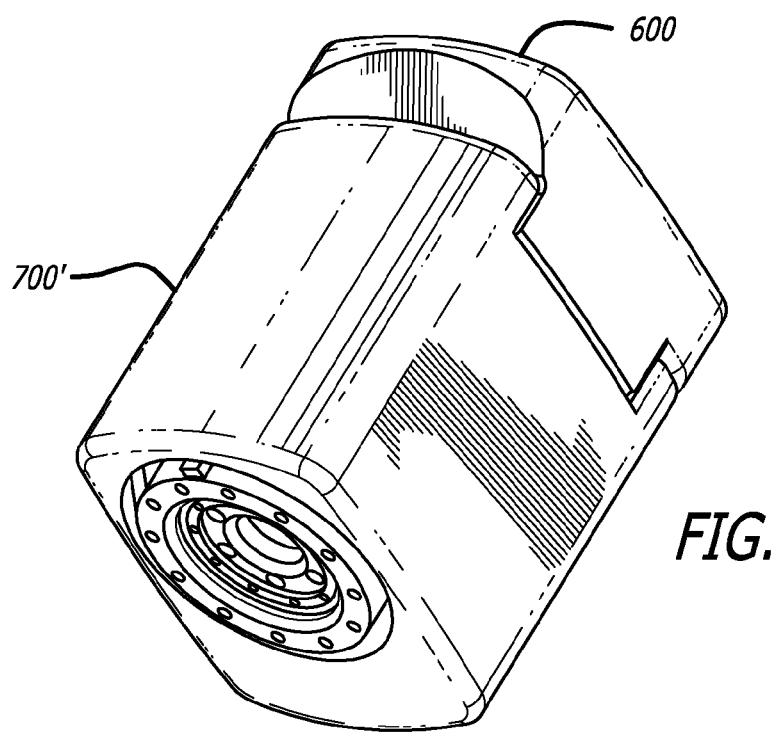
FIGS. 8A-8B illustrate views of the setup joint bracket of FIGS. 6A-6B coupled to the drive mount of FIG. 7B.
Figure 8B:
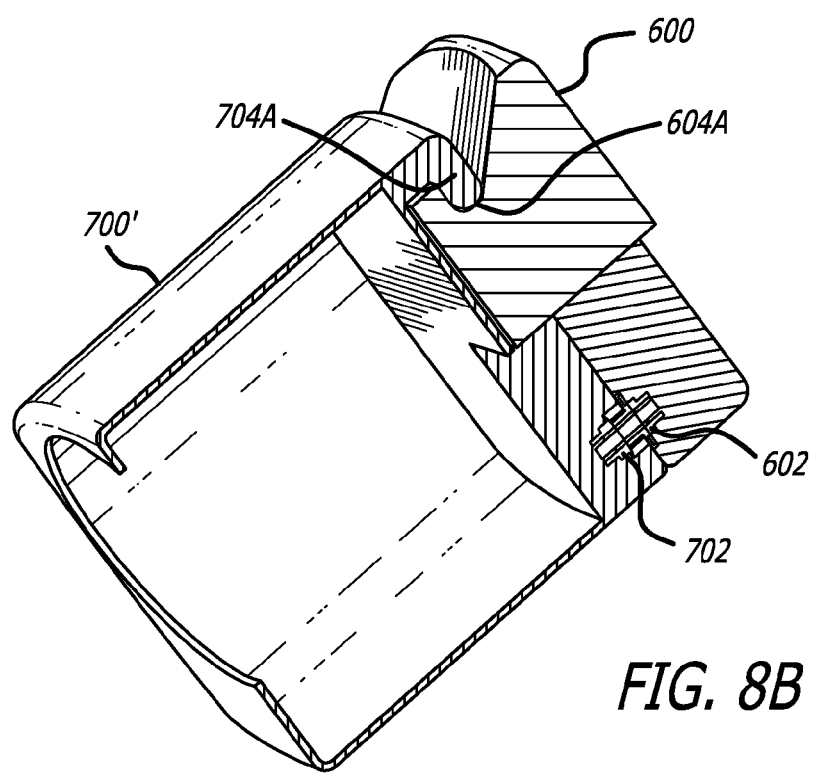

Referring now to FIGS. 8A-8B, the drive mount 700' is illustrated as being coupled to the setup joint bracket 600. A latch on one or more sides of each of the drive mount 700' and setup joint bracket 600, such as latch 800 illustrated in FIGS. 12A-12B, may be used to rigidly couple the two together. For example, a single latch may be used on a bottom side in one embodiment of the invention while a pair of latches may be used one on a left side and another on a right side in another embodiment of the invention. In this manner only one person may be needed to hang the robotic surgical arm and its drive mount 700,700' onto the setup joint bracket 600 of the set-up arm, and allow him/her to connect and lock it down with the one or more latches.

FIG. 8B better illustrates the mechanical interface between the hook 604A and the hooks 704A of the setup joint bracket 600 and the drive mount 700', respectively. FIG. 8B also better illustrates the electrical connection made between the electrical connectors 702 and 602 of the drive mount 700' and the setup joint bracket 600, respectively.

Figure 9A:
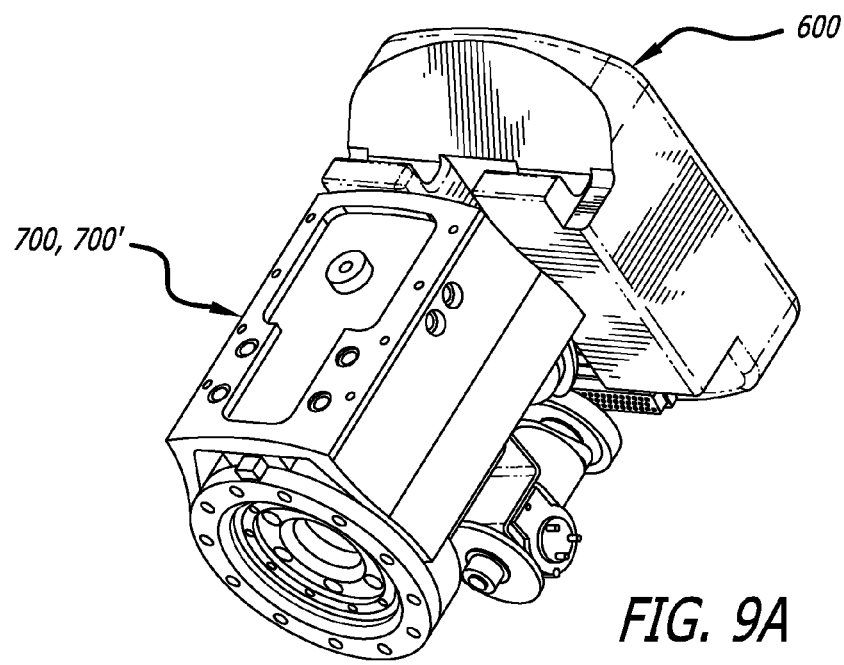
FIGS. 9A-9B illustrate views of the drive mount coupled to the setup joint bracket without its housing.
Figure 9B:
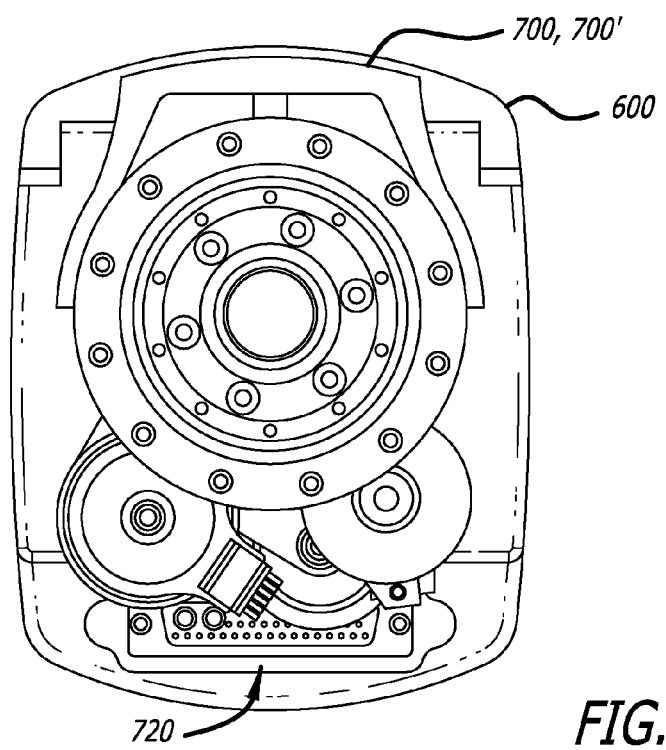

FIGS. 9A-9B illustrate the drive mount 700,700' coupled to the setup joint bracket 600 but with the housing of the drive mount 700,700' not illustrated. FIG. 9B illustrates where a cable bundle path 720 to the electrical connector 702 would be provided in the drive mount 700,700'.

Referring now to FIG. 10, the electrical connectors 602 and 702 are illustrated coupled together. The electrical connector 702 of the robotic surgical arm mates with the electrical connector 602. The electrical connector 602 in the setup joint bracket 600 includes floating bushings 630 to allow it to move and better mate with the electrical connector 702 in the drive mount 700,700', in one embodiment of the invention. In this case, the setup joint's electrical connector 602 may also be referred to as a floating electrical connector.

As shown in FIG. 10, the electrical signal pins 616S (see FIG. 6B) of the electrical connector 602 mate with the electrical signal pins 716S (see FIG. 7A) of the electrical connector 702. The electrical power pins 616P (see FIG. 6B) of the electrical connector 602 mate with the electrical power pins 716P (see FIG. 7A) of the electrical connector 702.

The mating of the electrical connectors 602 and 702 and their respective electrical signal pins 616S and 716S may provide one or more control signals to control one or both of the motors 401,402. The mating of the electrical connectors 602 and 702 and their respective power pins 616P and 716P may provide power and/or ground to one or both of the motors 401,402.

Referring now to FIG. 11, the replaceable hook 704 is illustrated isolated from the drive mount 700. The replaceable hook 704 of the drive mount 700 is made out of stainless steel in one embodiment of the invention and can be made thin, small and light. As illustrated in FIG. 11, the replaceable hook 704 includes a rolled edge 711 to facilitate pivoting within the one or more hooks 604. The hook 704 is fastened to the drive mount 700 by one or more fasteners 708, such as illustrated in FIG. 7A. As the hook 704 may sustain wear as it pivots in the one or more hooks 604 of the setup joint bracket, the fasteners 708 may be removed and a worn hook replaced with a new hook.

Referring now to FIG. 12A, a cut-away side view of the setup joint bracket 600 coupled to the drive mount 700,700' is illustrated. An over center latch 800 is coupled between the setup joint bracket 600 and the drive mount 700,700'. As shown better in FIG. 12B, the over center latch 800 includes a keeper 802 coupled to the setup joint bracket 600. The main portion of the over center latch 800 is coupled to the drive mount 700,700'. In which case, the main portion 804 of the latch 800 is retained with the drive mount 700,700' of the surgical arm. In this manner, it is easy for the over center latch 800 to be latched by a single user.

In summary, an interface at an end of the robotic surgical arm 158 is equipped with a bracket which has a "hook feature" provided by a hook 704 oriented or facing downward. An interface at an end of the set-up arm 156 is equipped with a mating hook feature provided by one or more hooks 604A-604B that are oriented or facing upward. The one or more hooks 604A-604B have a chamfer 611 above them in the interface of the set-up arm to provide space for the robotic surgical arm to mount and pivot the hook 704 within the one or more hooks 604A-604B.

An exemplary operation of the hook and pivot electromechanical interface for robotic surgical arms is now briefly described.

A person installing a robotic surgical arm is able to hang an end of the robotic surgical arm onto the set-up arm without much precision so that some of the weight of the robotic surgical arm is supported by the set-up arm. The robotic surgical arm may be more or less level when it is initially hung onto the set-up arm. The downward facing hook 704 of the drive mount 700,700' is mounted into the one or more upward facing hooks 604A-604B of the setup joint bracket 600. The downward facing hook 704 has a rounded lower edge which engages the one or more upward facing hooks 604A-604B of the set-up arm.

As the robotic surgical arm is lowered, the hung end pivots around the mated hooks 704 and 604A-604B. The tapered key feature (centered tapered key 710 and opening/slot 610) initially provides a coarse alignment between the robotic surgical arm and the set-up arm as the two parts are mated together. The pivoting action of the robotic surgical arm forces the tapered key 710 of the robotic surgical arm into the slot 610 of the set-up arm (these features may be on opposite sides such that tapered key 710 may be in the set-up arm while the slot 610 is in the robotic surgical arm) which progressively aligns the robotic surgical arm and the set-up arm by forcing it side-to-side until they are aligned. The key brings the two parts into close alignment (e.g., ½ mm approximately) so that the pair of blind-mate electrical connectors 602 and 702 (one equipped with tapered alignment pins) can start to align and mate.

Gravity may help to pivot the robotic surgical arm further downward continuing to drive the key 710 in further into the slot 610 and complete the alignment and mating of the electrical connectors. Once the robotic surgical arm is fully seated, a fastener, such as a latch or alternatively a bolt/screw, may be used to lock the connection together.

The quick-disconnect/connect interface between the robotic surgical arm and the set-up arm has the following features. The initial alignment precision between the robotic surgical arm and the set-up arm can be relatively low. The alignment precision between the robotic surgical arm and the set-up arm is progressively increased by the mechanical "wedging" of the key 710 into the slot 610 without a user having to fuss over the alignment. The weight of the robotic surgical arm is used to assist in making the connection between the robotic surgical arm and the set-up arm. The weight of the robotic surgical arm may provide the majority of the force for mating the electrical connectors 602 and 702 at the end of the stroke. The electrical connectors 602 and 702 are "blind mate" style electrical connectors with one having alignment pins to compensate for unit-to-unit mechanical tolerances, in one embodiment of the invention. The "mate-mechanical-before-electrical" design philosophy of the interface is used to reduce the risk of smashing the pins of the electrical connector during the initial alignment phase. When detaching the robotic surgical arm, the length/size of the robotic surgical arm acts as a giant "lever" to disengage the electrical connectors 602 and 702 from each other as they can mate with considerable force.

Conclusion

It is advantageous to be able to quickly, reliably and rigidly attach and remove items that have both mechanical and electrical connections. This is especially valuable for robotic surgical arms, where time to replace a robotic surgical arm is desirable to be kept to a minimum. Previously, making mechanical and the electrical connections simultaneously together meant that any misalignment of the mechanical connection could result in damage of the electrical connections, especially considering the tight tolerances required by most electrical connectors. The embodiments of the invention allow for the electrical connections to occur passively, after alignment of the mechanical elements and the mechanical connection is made, to avoid damage to the electrical connections.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art after reading this disclosure. For example, the embodiments of the invention have been described with reference to robotic surgical arms and robotic surgical systems. However, the embodiments of the invention are equally applicable to other types of robotic arms and robotic systems including robotic medical arms and robotic medical systems. Instead, the embodiments of the invention should be construed according to the claims that follow below.

What is claimed is:

1. A robotic medical system, comprising:
a detachable robotic medical arm to maneuver a tool, the detachable robotic medical arm including a first interface having
a first hook in a top portion of the first interface,
a tapered alignment protrusion, and
a first electrical connector below the first hook and the tapered alignment protrusion;
a set-up arm to support the detachable robotic medical arm, the set-up arm including a second interface to couple to the first interface of the detachable robotic medical arm, the second interface having
a second hook in a top portion of the second interface,
a chamfer above the second hook,
an alignment recess adapted to couple with the tapered alignment protrusion,
a second electrical connector below the chamfer, second hook, and alignment recess,
wherein the first hook to directly link to and pivot about the second hook to couple the detachable robotic medical arm to the set-up arm.

2. The robotic medical system of claim 1, wherein the first hook is a downward oriented hook; and
the second hook is an upward oriented hook.

3. The robotic medical system of claim 1, wherein the first hook is an upward oriented hook; and
the second hook is a downward oriented hook.

4. The robotic medical system of claim 1, wherein the alignment recess is an opening and
the tapered alignment protrusion is a tab.

5. The robotic medical system of claim 1, wherein the second interface of the set-up arm further includes a third hook parallel to the second hook separated by the alignment recess; and
the first hook is adapted to link and pivot with respect to the second and third hooks to couple the robotic medical arm to the set-up arm.

6. The robotic medical system of claim 1, wherein the second interface of the set-up arm further includes a third hook parallel to the second hook separated by the alignment recess;
the first interface of the robotic medical arm further includes a fourth hook parallel to the first hook separated by the tapered alignment protrusion; and
the first and fourth hooks are adapted to link and pivot with respect to the second and third hooks to couple the robotic medical arm to the set-up arm.

7. The robotic medical system of claim 1, wherein the first electrical connector is located in a bottom portion of the first interface opposite the top portion of the first interface;
the second electrical connector is located in a bottom portion of the second interface opposite the top portion of the second interface; and
the first hook is adapted to link and pivot with respect to the second hook to couple the first electrical connector of the robotic medical arm with the second electrical connector of the set-up arm.

8. The robotic medical system of claim 7, wherein the first electrical connector is movable with respect to the first interface to facilitate the mating of the first electrical connector to the second electrical connector.

9. The robotic medical system of claim 7, wherein the second electrical connector is movable with respect to the second interface to facilitate the mating of the second electrical connector to the first electrical connector.

10. The robotic medical system of claim 7, wherein the first and second electrical connectors are movable with respect to the first and second interfaces to facilitate the mating of the first electrical connector to the second electrical connector.

11. The robotic medical system of claim 10, wherein the first and second electrical connectors are linearly movable with respect to the first and second interfaces.

12. The robotic medical system of claim 1, further comprising:
a fastener to secure the first interface to the second interface.

13. The robotic medical system of claim 12, wherein the fastener is one or more bolts.

14. The robotic medical system of claim 12, wherein the fastener is a latch.

15. The robotic medical system of claim 7, wherein the first interface includes a motor for moving the robotic medical arm.

16. The robotic medical system of claim 15, wherein the motor is adapted to receive power and/or control signals by way of the first and second electrical connectors.

17. The robotic medical system of claim 7, wherein the robotic medical arm includes
a plurality of links serially connected to each other by way of one or more pivotable joints, respectively;
a drive train to pivot the plurality of links with respect to each other about the one or more pivotable joints; and
wherein the drive train is adapted to receive power and/or control signals by way of the first and second electrical connectors.

18. A detachable robotic medical arm, comprising:
a plurality of links pivotally coupled together in series to maneuver a tool;
a first motor coupled to at least one of the plurality of links to pivot the plurality of links; and
a drive mount pivotally coupled to a first link of the plurality of links, the drive mount having an electro-mechanical interface at a first end of the drive mount, the electro-mechanical interface including
one or more first hooks,
a first electrical connector positioned in different portions of the electro-mechanical interface, and
a tapered alignment protrusion adjacent to the one or more first hooks;
wherein the one or more first hooks to hook directly onto and pivot in one or more second hooks of a setup joint bracket of a set-up arm, the setup joint bracket to include a chamfer above the one or more second hooks, the tapered protrusion to align with and insert into a slot in the setup joint bracket, the first electrical connector to mate with a second electrical connector of the setup joint bracket of the set-up arm to provide one or more control signals to control the first motor.

19. The detachable robotic medical arm of claim 18, wherein
the first electrical connector is further configured to mate with the second electrical connector of the setup joint bracket of the set-up arm to provide power to the first motor.

20. The detachable robotic medical arm of claim 18, wherein
the drive mount further has a second electrical motor to pivot the plurality of links; and the first electrical connector further to mate with the second electrical connector of the setup joint bracket of the set-up arm to provide control signals to control the second motor.

21. The detachable robotic medical arm of claim 18, wherein
the drive mount further has a latch to couple to a keeper of the setup bracket to rigidly couple the robotic medical arm to the set-up arm.

22. The detachable robotic medical arm of claim 18, wherein the first electrical connector of the drive mount has a pair of tapered alignment pins to couple into a pair of alignment holes in the second electrical connector of the setup bracket to align the first and second electrical connectors together.

\* \* \* \* \*